United States Patent
Linev et al.

(10) Patent No.: US 11,762,123 B2
(45) Date of Patent: Sep. 19, 2023

(54) X-RAY CROSS TECHNOLOGY FOR HUMAN BODY INSPECTION

(71) Applicant: ADANI Systems, Inc., Alexandria, VA (US)

(72) Inventors: Vladimir N. Linev, Minsk (BY); Dzmitryi Bairashewski, Minsk (BY)

(73) Assignee: Linev Systems US, Inc., Alexandria, VA (US)

(*) Notice: Subject to any disclaimer, the term of this patent is extended or adjusted under 35 U.S.C. 154(b) by 67 days.

(21) Appl. No.: 17/668,214

(22) Filed: Feb. 9, 2022

(65) Prior Publication Data

US 2023/0251397 A1 Aug. 10, 2023

(51) Int. Cl.
*G01V 5/00* (2006.01)
*A61B 6/00* (2006.01)
*A61B 6/06* (2006.01)
*A61B 6/03* (2006.01)

(52) U.S. Cl.
CPC ............ *G01V 5/0066* (2013.01); *A61B 6/032* (2013.01); *A61B 6/06* (2013.01); *A61B 6/4452* (2013.01); *A61B 6/4476* (2013.01)

(58) Field of Classification Search
CPC ........ G01V 5/0066; A61B 6/032; A61B 6/06; A61B 6/4452; A61B 6/4476
See application file for complete search history.

(56) References Cited

U.S. PATENT DOCUMENTS

| | | | |
|---|---|---|---|
| 2007/0086566 A1* | 4/2007 | Gregerson | A61B 6/4405 378/19 |
| 2011/0080994 A1* | 4/2011 | Hoffman | A61B 6/4233 378/19 |
| 2011/0080995 A1* | 4/2011 | Hoffman | G01T 1/2985 378/19 |
| 2013/0136231 A1* | 5/2013 | Cox | G01V 5/0016 378/62 |
| 2013/0202087 A1* | 8/2013 | Cox | G01N 23/04 378/62 |
| 2015/0177391 A1* | 6/2015 | Cox | G01N 23/04 378/62 |
| 2017/0124731 A1* | 5/2017 | Gregerson | G06T 7/0012 |
| 2022/0240885 A1* | 8/2022 | Chen | A61B 6/582 |

* cited by examiner

*Primary Examiner* — David P Porta
*Assistant Examiner* — Casey Bryant
(74) *Attorney, Agent, or Firm* — Bardmesser Law Group

(57) ABSTRACT

An X-ray scanner includes a frame; an X-ray generator mounted within the frame, and outputting a vertical fan-shaped beam toward an object; the X-ray generator configured to rotate in a left-right direction; a linear vertical X-ray detector mounted in the frame beyond the object, the linear vertical X-ray detector configured to slide in sync with a rotation of the X-ray generator; a first flat panel X-ray detector below the object, the first flat panel X-ray detector being stationary; a second flat panel X-ray detector above the object, the second flat panel X-ray detector being stationary; a workstation that integrates scans from the first flat panel X-ray detector, the second flat panel X-ray detector and the linear vertical X-ray detector to generate a full-body scan of the object.

7 Claims, 10 Drawing Sheets

X-RAY CROSS TECHNOLOGY FOR HUMAN BODY INSPECTION

BACKGROUND OF THE INVENTION

Field of the Invention

The present invention relates to technology of generating X-ray images of a human body by an X-ray scanner, and, more particularly, combining the technologies of narrow-beam scanning by a linear detector and simultaneous exposure using a flat X-ray sensitive imager.

Description of the Related Art

Technologies that can be used for X-ray scanning of the human body have long been limited by ANSI 43.17-2009 radiation safety requirements, the range of X-ray detection solutions, and their high price.

The most effective solution was one, in which the human body is scanned by a flat fan-like X-ray beam detected by a linear X-ray detector. The person is moved either while standing on a moving platform or on a conveyor belt through a static X-ray beam. This conventional solution that uses a static X-ray beam has a number of drawbacks.

The detector and beam have to be calibrated extremely precisely, since even the slightest deviation may cause the image quality to deteriorate. Meanwhile, calibration is rigidly mechanical and thus can be easily distorted by a mechanical impact.

These distortions can be less critical, if the X-ray source is stationary, and the person is being moved through the beam instead. However, the scanning time should be at least 5-10 seconds, since the scanned person may fall from the moving platform if it moves too fast.

On the other hand, calibration distortions become more critical, if the person stands still, and the mechanical frame is moving around them. In addition, such mechanical frames are difficult to assemble and are too large to be transported though doorways.

The objective of the proposed invention is to minimize the drawbacks of the conventional scanning technology that uses a static beam and improve performance of human body scanning systems while conforming to ANSI 43.17-2009 requirements.

SUMMARY OF THE INVENTION

In the first aspect of the present invention, the conventional scanning technology, in which a linear X-ray detector is moving simultaneously with the X-ray beam, is combined with a technology, in which the scanning beam is moving along a flat-panel X-ray sensitive high-resolution imager. The system includes two X-ray sensitive imagers (flat panel detectors) and one linear detector oriented vertically. One of the two flat panel imagers is used to obtain an X-ray image of the feet, and the other one is used to obtain an X-ray image of the head. The linear detector is used to obtain an X-ray image of the body, without the head and feet. During the scanning, the X-ray beam is moving along the X-ray sensitive panels simultaneously with the linear detector. The resulting X-ray image includes three X-ray images in total: two from the flat panels and one from the linear detector.

In the second aspect of the present invention, the X-ray source and linear detector are not connected mechanically, and their simultaneous movement is controlled by software.

In order to move the assembled detector, an actuator frame is proposed. The actuator frame comprises a toothed belt drive, a planetary reduction drive, and a synchronous motor. There is no direct gauge in the actuator frame, therefore, its positioning is controlled by a motor sensor of absolute measurement. The positioning of the detector is controlled by a two-axis inclinometer.

The X-ray generator is mounted on the swivel actuator comprising a planetary reduction drive, a bellows coupling, a radial thrust bearing, and a synchronous motor. There is no direct gauge in the swivel actuator, therefore, its positioning is controlled by a motor sensor of absolute measurement. The positioning of the X-ray generator rotation axis is controlled by a two-axis inclinometer.

The simultaneous movement (coordinates) is controlled by a controller.

Another optional aspect of the invention involves limiting the scan area to as low as 500 mm×500 mm, using a special shielding mechanism that includes shields that move up and down, so as to limit the vertical scan field to 500 mm. The horizontal scan field is limited to 500 mm by limiting the rotation of the X-ray generator. Based on the ANSI 43.17-2009 standard, this makes the scanner a class B scanner, which permits different operating modes for the generator while maintaining safety requirements, as required by ANSI 43.17-2009. Thus, a more powerful generator can be used, with a corresponding improvement in resolution and detection.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED FIGURES

The accompanying drawings, which are included to provide a further understanding of the invention and are incorporated in and constitute a part of this specification, illustrate embodiments of the invention and, together with the description, serve to explain the principles of the invention.

DETAILED DESCRIPTION OF EMBODIMENTS OF THE INVENTION

Figure 1:
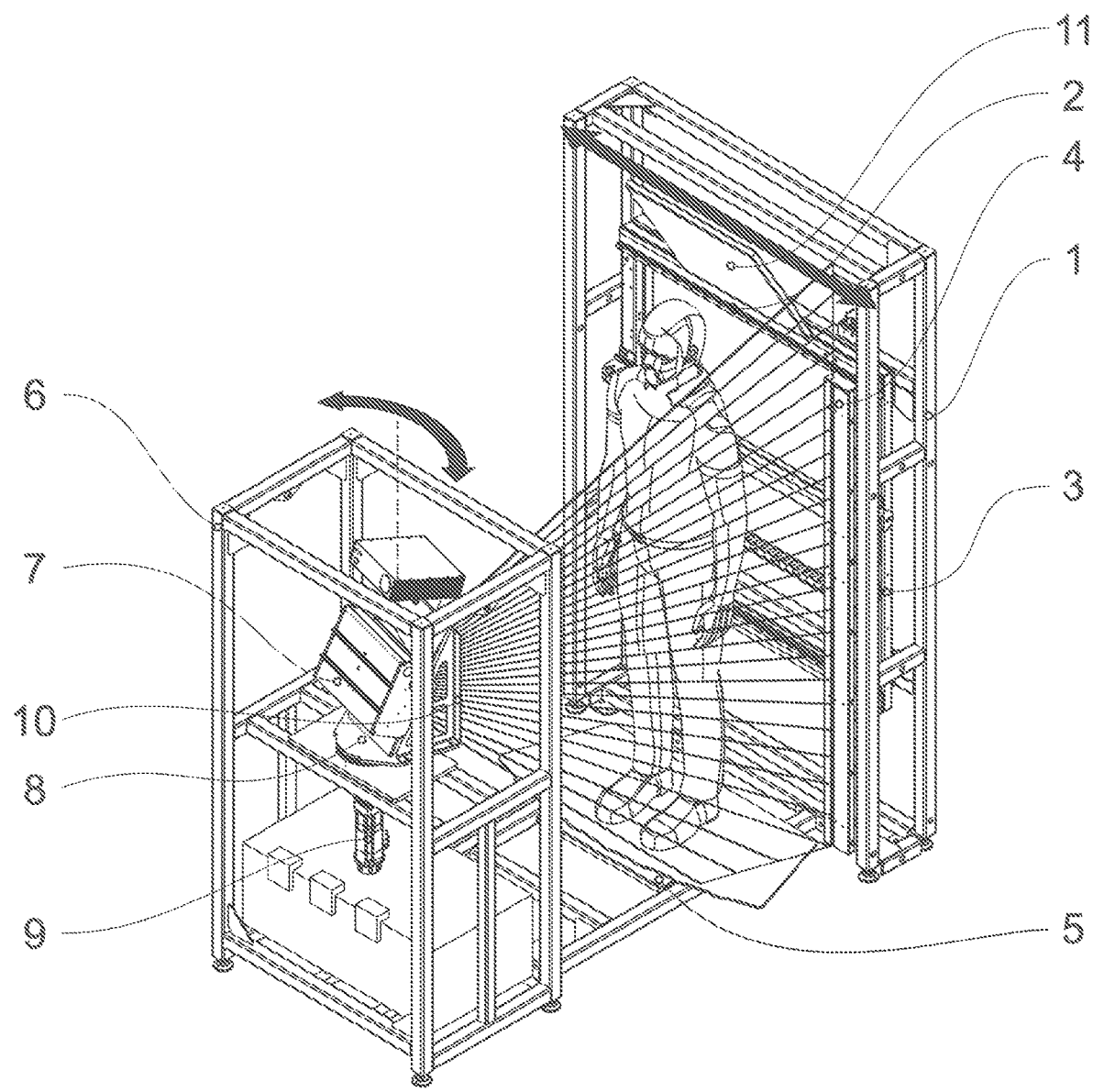
FIGS. 1-3 show 3D perspective views of the scanner of the present invention.
Figure 2:
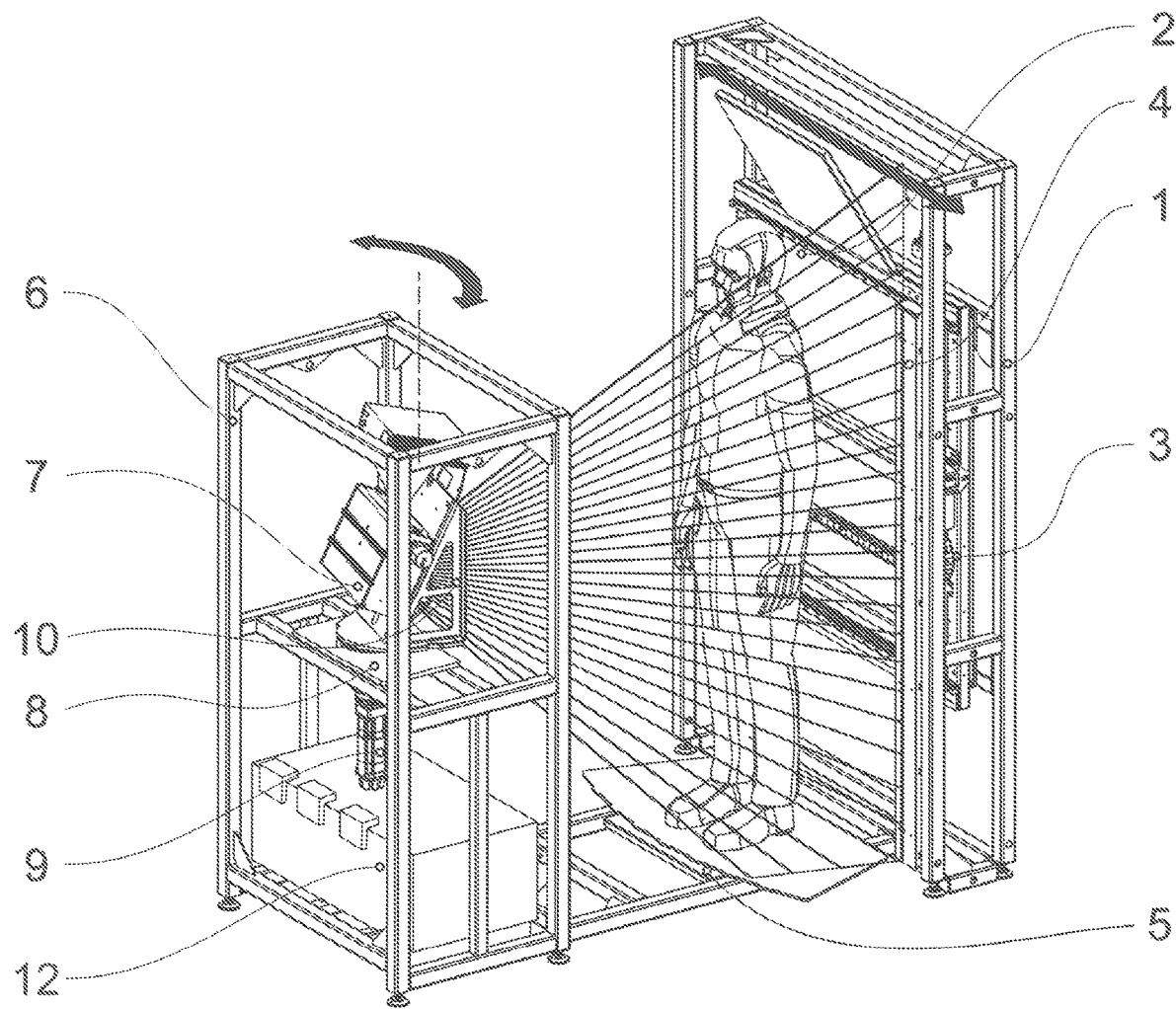
Figure 3:
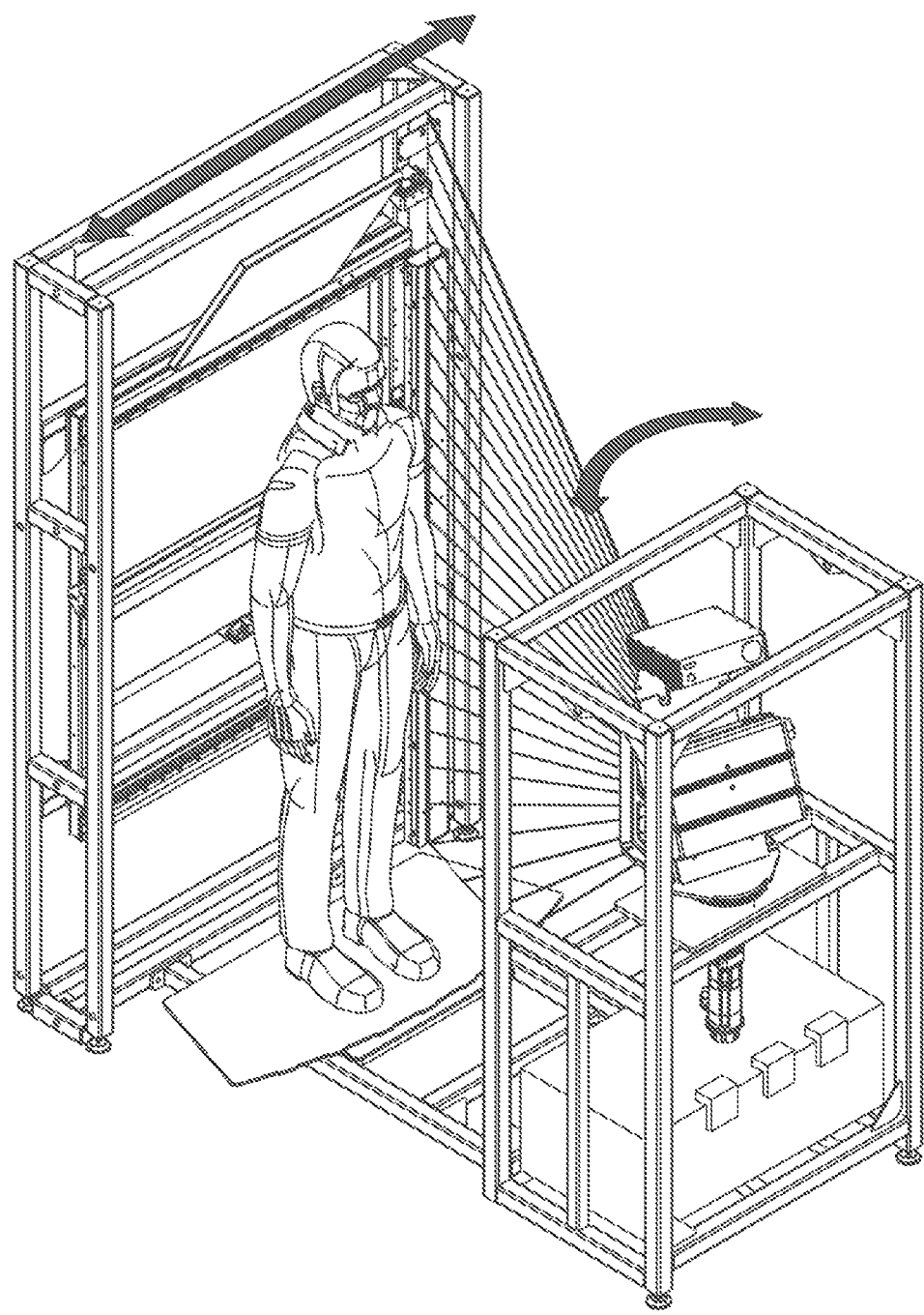
Figure 4:
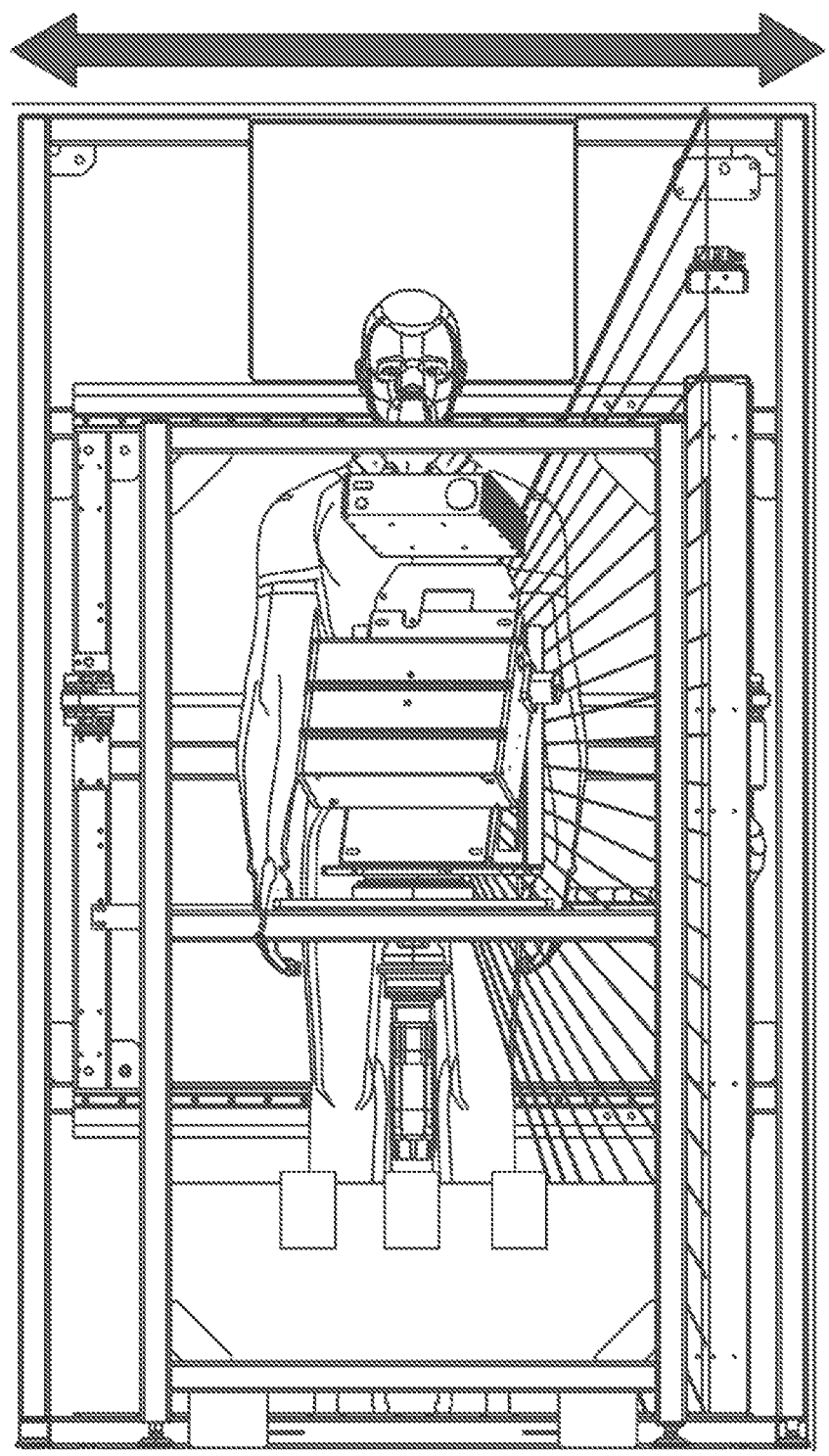
FIG. 4 shows a front view of the scanner of the present invention.
Figure 5:
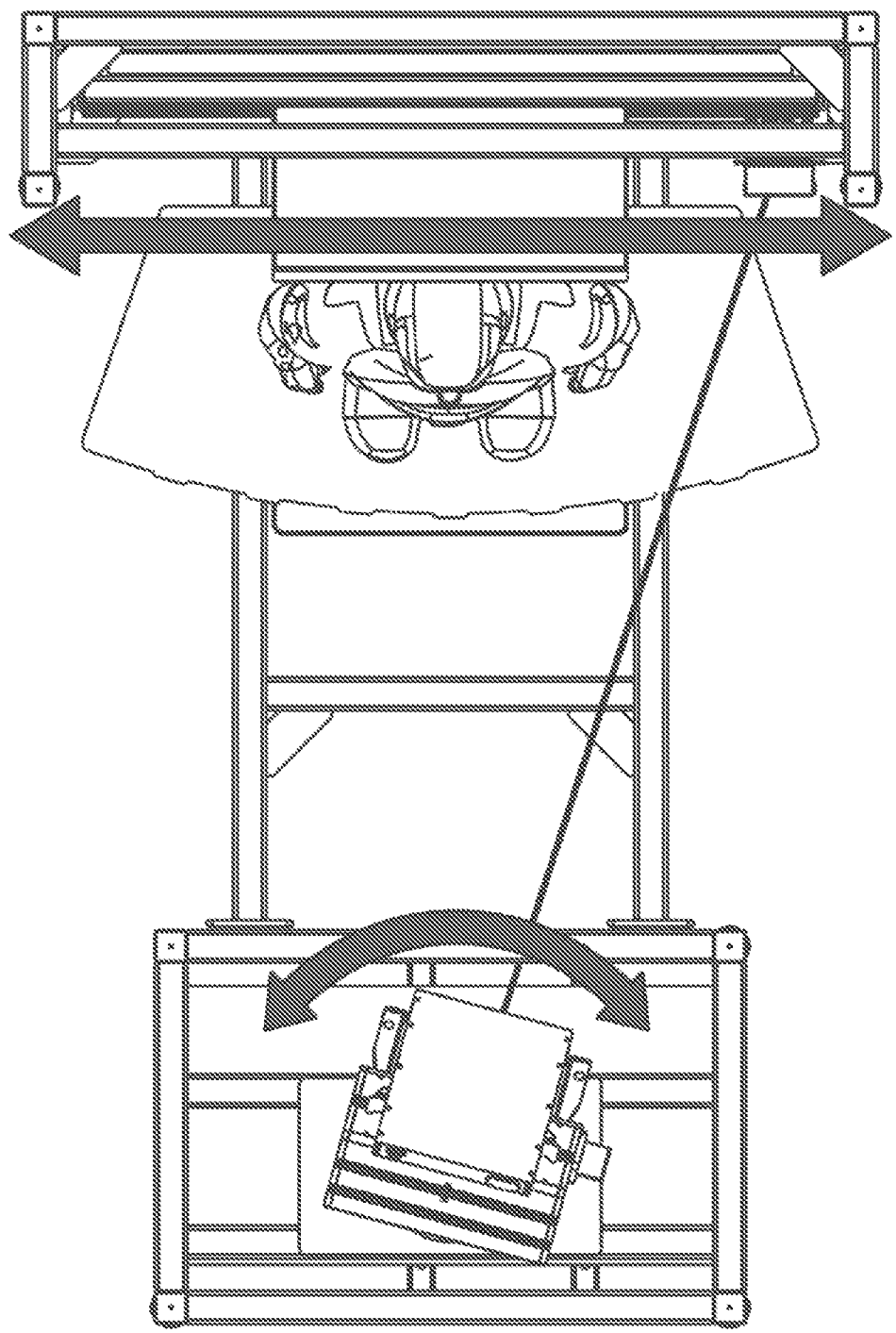
FIG. 5 shows a top view of the scanner of the present invention.

Reference will now be made in detail to the preferred embodiments of the present invention, examples of which are illustrated in the accompanying drawings.

The proposed scanner includes two main modules, see FIGS. 1-6, illustrating various views of the scanner: an X-ray generation cabinet (6) and an X-ray detector cabinet (1).

The X-ray generation cabinet (6) includes an X-ray generator (7), a beam limiting device with X-ray protective shutter and collimator slit (10), a generator assembly swivel actuator (8), and a generator assembly swivel actuator gear-motor (9).

The X-ray detector cabinet (1) includes a linear X-ray detector (4) mounted on a linear detector actuator frame (2), and flat-panel detectors (5, 11) located at the feet and head levels, respectively.

The X-ray generator (7) revolves around a vertical axis that passes through the focus on the X-ray tube, and produces a narrow X-ray beam, which is 0.5-2 mm wide and covers a 1-pixel area when it hits the X-ray detector (4).

The X-ray detector (4) is mounted on the linear detector actuator frame (2) that is moved along a horizontal axis by a linear detector actuator gear-motor (3) past a control object, so that the moving beam covers the entire surface of the X-ray detector (4) all the time. Flat-panel detectors (5, 11) remain stationary in order to generate a high-resolution X-ray image of the head and feet.

The X-ray generator (7) and the linear detector actuator frame (2) are not connected mechanically, but their movement is synchronized. The positions of the X-ray generator (7) and the X-ray detector (4) are adjusted automatically based on the detector's signal level.

The control object is placed above the flat-panel detector (5) as shown, between the X-ray generation cabinet (6) and the X-ray detector cabinet (1). The scanned person has to stand still during scanning. The X-ray beam passes through the control object and hits the X-ray detector (4) and the flat-panel detectors (5, 11), thus creating an X-ray image of the scanned person.

The X-ray generator can be implemented in a single module and operates within the range of up to 200 kV of anode voltage, which provides enough excitation for the X-rays to pass through the human body. The X-ray generator power ranges between 200 W and 500 W. Thanks to an X-ray limiter, this power allows to provide a scanning radiation dose that meets the international safety standards—ANSI43.17-2009 in particular. The X-ray generator (7) is revolved (rotated) by a swivel actuator comprising a planetary reduction drive, a bellows coupling, a radial thrust bearing, and a synchronous motor. All its movements are controlled by a programmable logical controller (12).

To ensure that the scanning area is sufficient to scan a human being, the working angle of rotation of the generator (7) around the vertical axis is typically 35-40 degrees. To avoid problematic situations involving rotation of the X-ray generator, various software and hardware restrictions on the rotation can be implemented. The software can limit the rotation to 40-45 degrees, which takes care of any assembly errors. Physical limits on rotation can be implemented through hard stops, where the frame prevents rotation of the generator (7) beyond 43-48 degrees.

The linear X-ray detector (4) is based on a set of boards mounted in a single row, so that the X-ray sensitive scintillator, in a single vertical line, could capture the entire X-ray fan beam hitting it. All the detector boards of the X-ray detector (4) are connected in series so that an output connection of each board is connected to the input connection of the next board in series.

The scintillator can be made up of a variety of X-ray sensitive materials having enough thickness to effectively capture photons that reach it. For example, a CsI scintillator can be used, with a pixel height 3.2 mm, and a pixel width 1.4 mm, and a pixel step of 1.5 mm. The linear X-ray detector continuously accumulates X-rays during a pre-set interval, known as integration time. The X-ray beams and energy captured by the detector are then converted into digital imaging data and sent to the data collection unit.

Flat-screen detectors (5, 11) located at the head and feet levels are made up of digital imagers with X-ray sensitive scintillators area 17"×17" in size or larger, with a pixel step of 100-200 microns. Flat-screen detectors are able to obtain X-ray images with better spatial resolution. Unlike linear X-ray detectors, flat-screen detectors require higher radiation power to obtain satisfactory X-ray images. Therefore, in order to keep radiation doses within the safety standards, such flat-screen detectors are located at the head and feet levels only, where more power reaches the detector.

Figure 6:
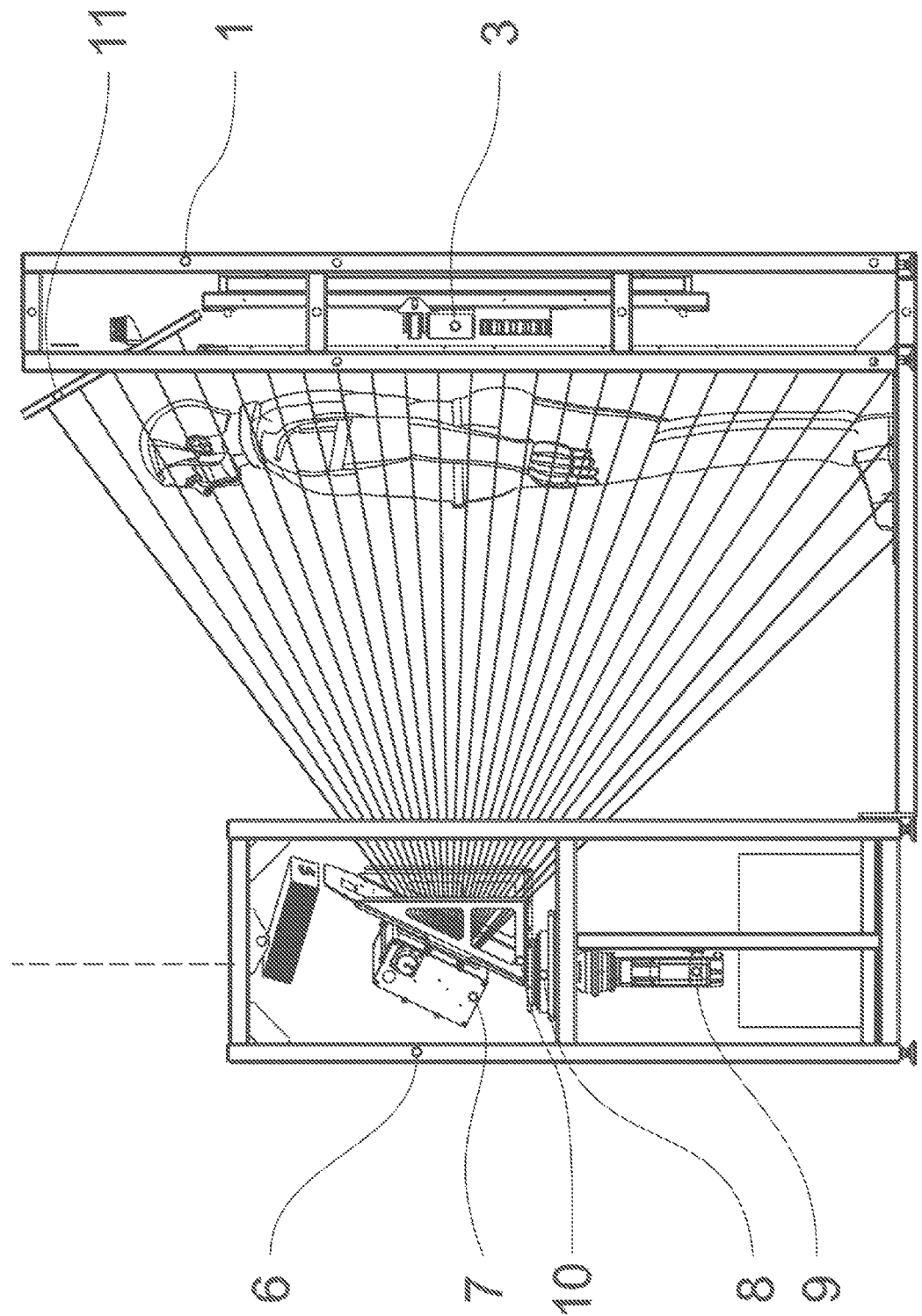
FIG. 6 shows a side view of the scanner of the present invention.
Figure 8:
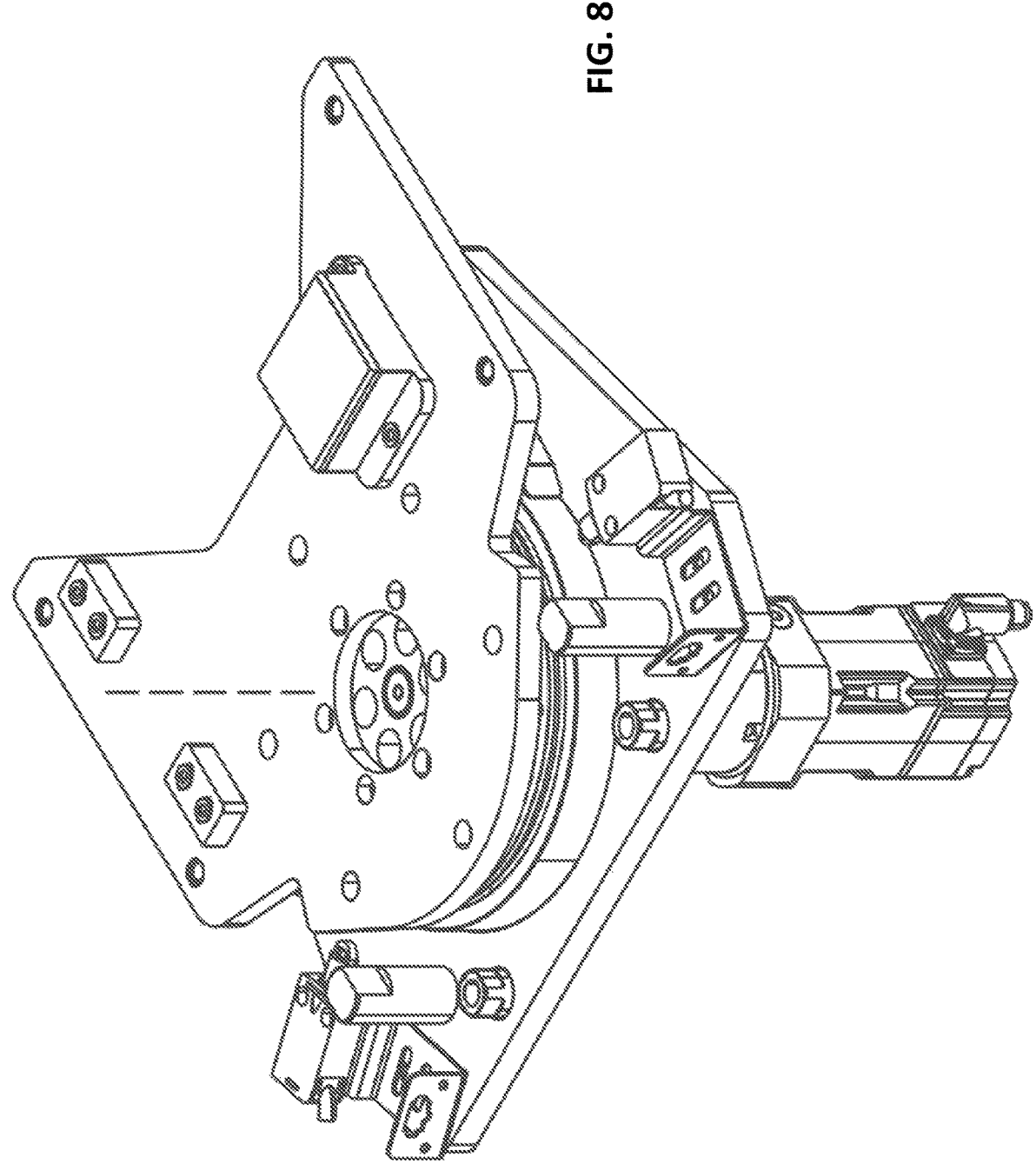
FIGS. 8 and 9 show perspective views of the motor assembly.
Figure 9:
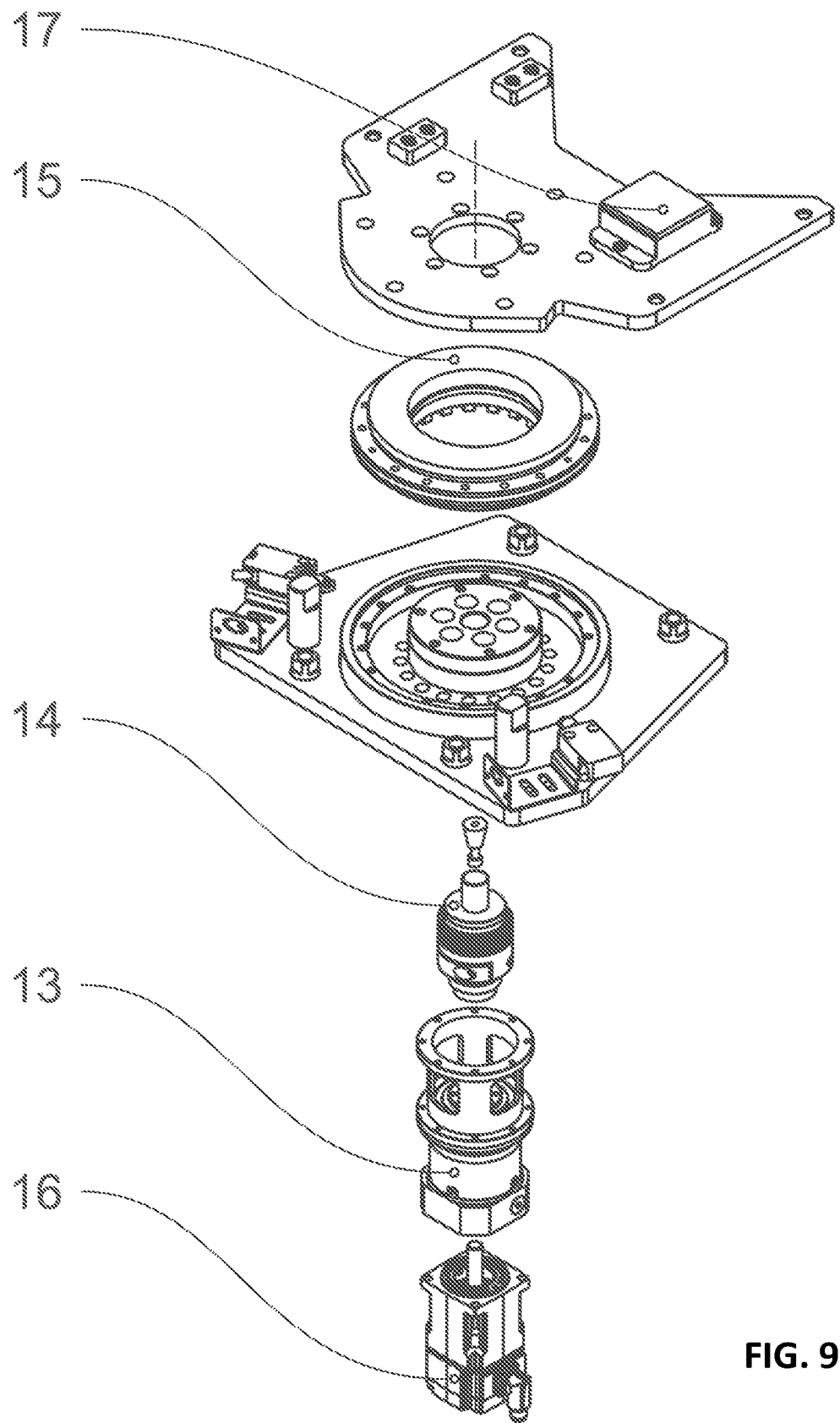

FIGS. 8 and 9 show perspective views of the motor assembly. FIG. 8 shows a mounting plate on which the X-ray generator is mounted. FIG. 9 shows the other components, such as the inclinometer 17, the planetary reduction drive 13, the bellows coupling 14, the radial thrust bearing 15 and the synchronous motor 16. The generator assembly swivel actuator gear-motor (9) shown in FIG. 6 is composed of the planetary reduction drive 13, the bellows coupling 14, the radial thrust bearing 15 and the synchronous motor 16. The angular position sensor is located inside the motor 16, and provides an output of the current position of the motor 16.

Figure 10:
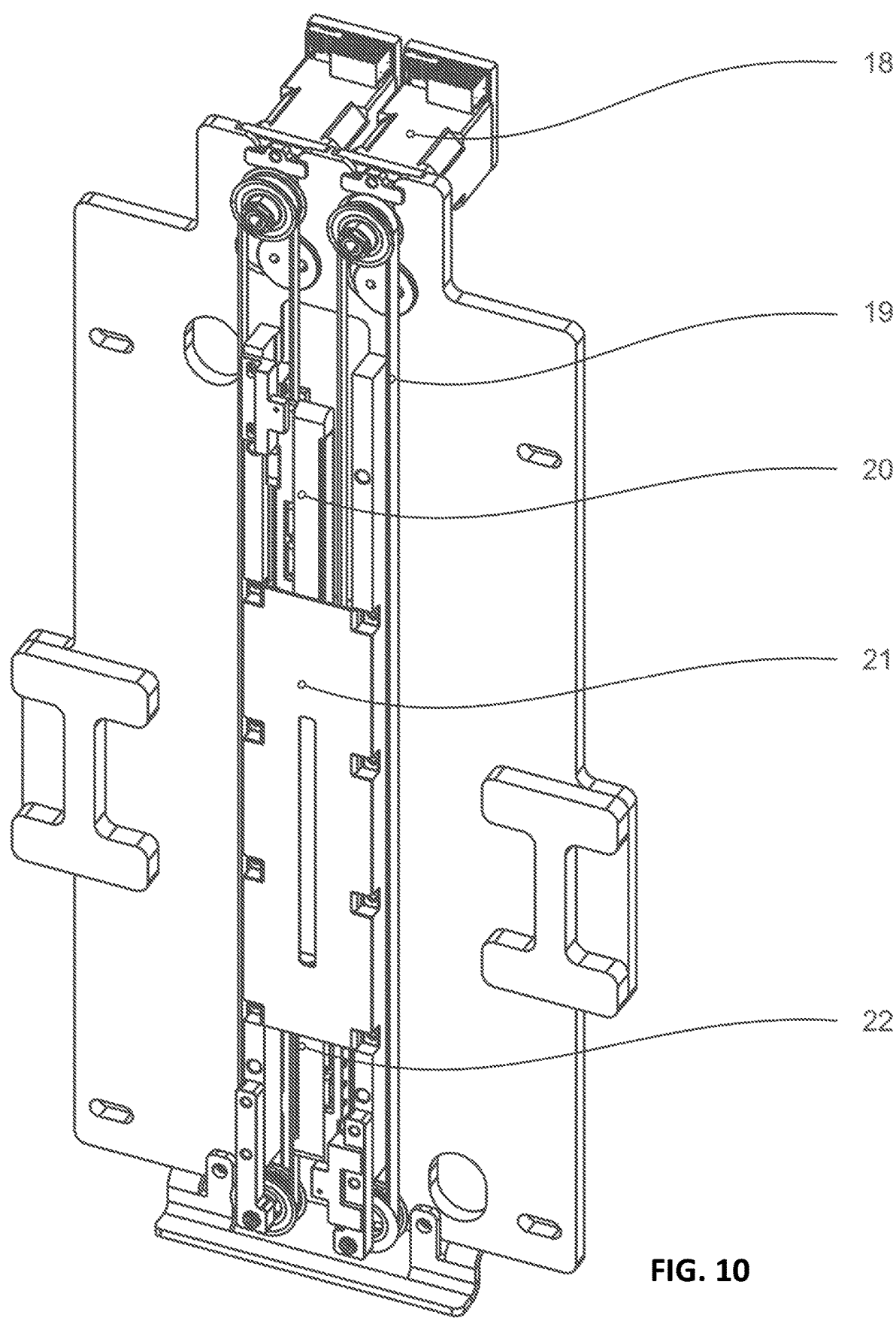
FIG. 10 illustrates the unit for moving the protective shielding.

FIG. 10 shows the unit for moving the protective shielding, which is responsible for limiting the field of scan in the vertical dimension to 500 mm. The unit includes a drive 18, a drive belt 19, an upper shield 20, a collimation window 21 and a lower shield 22.

The shields work as follows: the shields 20 and 22 are located behind the collimation window 21, and can limit the fan-shaped X-ray beam that passes through the collimation window 21. The position of the shields 20, 22 is changed by the drive 17, using the belts 19. If a beam that scans the entire person is needed, then the upper shield is moved as high as possible, and the lower shield is moved as low as possible. If a 500 mm region is needed to be scanned, the shields 20, 22 are positioned accordingly, so that only the zone of interest is scanned. The position of the shields is determined by an operator, using a desktop computer, and is controlled by the microcontroller.

Limiting the scan field to less than 500 mm in the horizontal direction is done by limiting the rotation of the X-ray generator to a corresponding angle. The synchronization of the rotation of the generator and the X-ray detector is done using a microcontroller, same as in the case of a full-body scan.

The ability to limit the scan field to 500×500 mm permits classifying this type of scan as a partial body scanner under class B (according to ANSI43.17-2009), which in turn permits improving the quality of the X-ray image and the detection ability due to improved output by the X-ray generator.

The synchronization of the rotation of the X-ray generator and the linear detector is based on signals received from the linear detector. First, the linear detector is held stationary in the center position and the X-ray generator is rotated until the signal strength is at a maximum. The system is calibrated by rotating the X-ray generator left and right in small incremental steps, to find the maximum. These values of linear detector location and X-ray generator rotation angle are used in the future for initial positioning of a scan.

The process is then repeated for other positions of the linear detector, in the left-right direction. Thus, for each point where the linear detector is positioned, there is a corresponding angle for the rotation of the X-ray generator. The controller (not shown in the figures) interpolates the speed of the movement of the linear detector between the points, so that the X-ray intensity remains at a maximum during the movement and the corresponding rotation of the X-ray generator. The greater the number of points where the linear detector is calibrated, the greater the accuracy and the stability of the signal. Note that the left-right motion of the vertical linear detector is non-linear in terms of its velocity (highest at the edges, slowest in the center).

Figure 7:
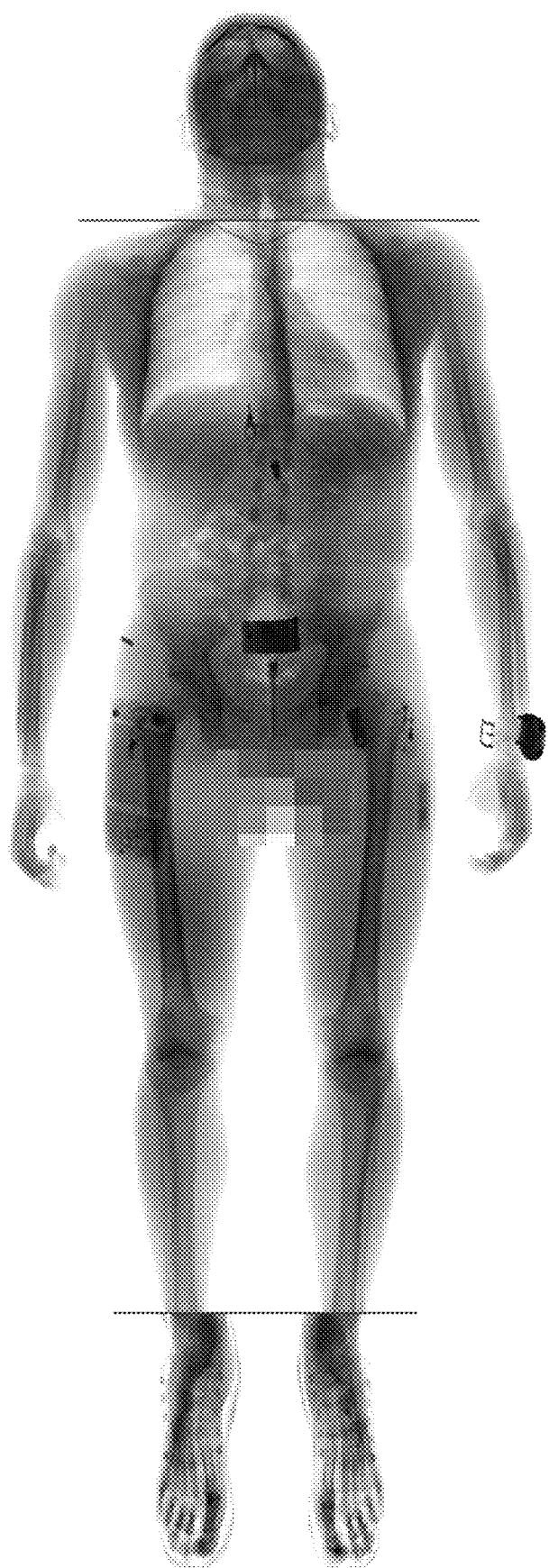
FIG. 7 shows three images being combined into a single image.

The resulting X-ray image of a human body is obtained by combining two images from the flat-screen detectors with an image from the linear detector. The images are combined automatically by software, after all three detectors have been calibrated by position and zoomed against each other. Such preliminary calibration can be done either manually or automatically during assembly, using a calibration object that occupies the entire field to be scanned by the detectors, see FIG. 7.

At the lower level, the components are controlled by a technological controller; at the upper level, they are controlled by software and an operator, using a PC connected to both the units of the invention and the technological controller.

X-ray images can be viewed and processed using specialized software and software mathematical algorithm running on a personal computer or similar (not shown in the figures).

The operator's workstation may have different embodiments. Depending on the location of the apparatus, it may be integrated into the X-ray generation cabinet or separated from the rest of the invention.

The advantages of the present invention are as follows:

1. The detector and generator are mechanically independent, which allows to adapt the system to the working environment and geometry.

2. The system calibrates automatically thanks to electromechanical synchronization and detector signal level analysis.

3. The system is modular, and each module can be transported separately.

4. The flat-panel detection technology allows to obtain high-resolution images of the head and feet. The full-body image comprises a single body image provided by the linear detector and two images of the head and feet, respectively, provided by the flat panel detectors.

5. The flat detector for scanning feet has low threshold values both at the input and output of the system, thus making the scanner conform to ADA requirements.

6. Scanned areas can be selected by using the linear X-ray detector (4) and flat panel detectors (5, 11) either separately or together.

Having thus described a preferred embodiment, it should be apparent to those skilled in the art that certain advantages of the described method and apparatus have been achieved. It should also be appreciated that various modifications, adaptations, and alternative embodiments thereof may be made within the scope and spirit of the present invention.

What is claimed is:

1. An X-ray scanner, comprising:
   a frame;
   an X-ray generator mounted within the frame, the X-ray generator outputting a vertical fan-shaped beam toward an object being scanned;
   the X-ray generator configured to rotate in a left-right direction;
   a linear vertical X-ray detector mounted in the frame beyond the object, the linear vertical X-ray detector configured to slide linearly left-right in sync with a rotation of the X-ray generator;
   a first flat panel X-ray detector below the object, the first flat panel X-ray detector being stationary;
   a second flat panel X-ray detector above the object, the second flat panel X-ray detector being stationary;
   a workstation that integrates scans from the first flat panel X-ray detector, the second flat panel X-ray detector and the linear vertical X-ray detector to generate a full-body scan of the object.

2. The X-ray scanner of claim 1, wherein the first flat panel X-ray detector is at least 17"×17".

3. The X-ray scanner of claim 1, wherein the second flat panel X-ray detector is at least 17"×17".

4. The X-ray scanner of claim 1, wherein the linear vertical X-ray detector includes a plurality of detector boards that are connected in series so that an output connection of each board is connected to the input connection of a next board, and
   Wherein each detector board includes a plurality of pixels with a pixel height 3.2 mm, a pixel width 1.4 mm, and a pixel step of 1.5 mm.

5. The X-ray scanner of claim 1, wherein the X-ray generator is mounted on a swivel actuator comprising a planetary reduction drive, a bellows coupling, a radial thrust bearing, and a synchronous motor.

6. The X-ray scanner of claim 5, wherein positioning of the swivel actuator is controlled by a motor sensor of absolute measurement.

7. The X-ray scanner of claim 5, wherein positioning of the X-ray generator's rotation axis is controlled by a two-axis inclinometer.

* * * * *